US009655962B2

(12) United States Patent
Mitteness et al.

(10) Patent No.: US 9,655,962 B2
(45) Date of Patent: May 23, 2017

(54) METHODS AND COMPOSITIONS FOR REDUCING MICROORGANISMS IN THE OROPHARYNX, NASOPHARYNX AND ORAL CAVITIES (71) Applicant: Camas Incorporated, Le Center, MN (US)

(72) Inventors: Bradley M. Mitteness, Ghent, MN (US); Connie Phillips, St. Peter, MN (US)

(73) Assignee: CAMAS INCORPORATED, Le Center, MN (US)

( * ) Notice: Subject to any disclaimer, the term of this patent is extended or adjusted under 35 U.S.C. 154(b) by 0 days.

(21) Appl. No.: 14/211,947

(22) Filed: Mar. 14, 2014

(65) Prior Publication Data
US 2014/0271501 A1 Sep. 18, 2014

Related U.S. Application Data (60) Provisional application No. 61/788,513, filed on Mar. 15, 2013.

(51) Int. Cl.
| A61K 39/395 | (2006.01) |
| A61K 39/40 | (2006.01) |
| A61K 9/00 | (2006.01) |
| C07K 16/12 | (2006.01) |
| C07K 16/14 | (2006.01) |
| A61K 39/00 | (2006.01) |

(52) U.S. Cl.
CPC .......... *A61K 39/395* (2013.01); *A61K 9/0012* (2013.01); *A61K 9/0063* (2013.01); *A61K 39/39575* (2013.01); *A61K 39/40* (2013.01); *C07K 16/1203* (2013.01); *C07K 16/1207* (2013.01); *C07K 16/1242* (2013.01); *C07K 16/1275* (2013.01); *C07K 16/14* (2013.01); *A61K 2039/505* (2013.01); *C07K 2317/11* (2013.01); *C07K 2317/23* (2013.01)

(58) Field of Classification Search
CPC .................................................. A61K 39/395
See application file for complete search history.

(56) References Cited

U.S. PATENT DOCUMENTS

| 5,610,011 | A  | * | 3/1997  | Smith et al.     | 435/6.13 |
| 6,245,789 | B1 | * | 6/2001  | Camden           | 514/365 |
| 8,372,393 | B2 |   | 2/2013  | Kundig et al.    |          |
| 2005/0208078 | A1 | * | 9/2005  | Hoffman et al.   | 424/272.1 |
| 2006/0134101 | A1 | * | 6/2006  | Larsson et al.   | 424/133.1 |
| 2006/0171960 | A1 |   | 8/2006  | Chu et al.       |          |
| 2007/0087029 | A1 |   | 4/2007  | Pakala           |          |
| 2011/0274701 | A1 |   | 11/2011 | Mitteness et al. |          |

FOREIGN PATENT DOCUMENTS

WO  2013009843 A1  1/2013

OTHER PUBLICATIONS

Plotkin et al (Vaccines WB Saunders Company, p. 571, 1988).*
Smith et al (Infection and Immunity vol. 69, No. 5, pp. 3135-3142, 2001).*
Vanier et al. (2006) "Haemophilus parasuls invades porcine brain microvascular endothelial cells". Microbiology 152: 135-142.
Gottschalk et al, (1995) "Characterization of *Streptococcus suis* capsular type 2 haemolysin", Microbiology 141: 189-195.
Dominguez-Punaro et al. (2008) "Comparison of the Susceptibilities of C57BL/6 and A/J Mouse Strains to *Streptococcus suis* Serotype 2 Infection", Infection and Immunity 76: 3901-3010.
Zheng et al. (2009) "Pathologic Analysis of the Brain from *Streptococcus suis* Type 2 Experimentally Infected Pigs", Vet Pathol 46: 531-535.
Vanier et al. (2004) "Invasion of Porcine Brain microvasuclar Endothelial Cells by *Streptococcus suis* Serotype 2", Infection and Immunity 72: 1441-1449.
Kaushik et al. (2003) "Why is Trehalose an Exceptional Protein Stabilizer?", Journal of Biological Chemistry. 278 29:36458-26465.
Carlander et al. (2002) "Retention of specific yolk IgY in the human oral cavity", BioDrugs 16(6): 433-437; Abstract.
Wright et al. (2010) "Interaction of *Staphylococci* with bone" International Journal of Medical Microbiology 300: 193-204.
Zheng et al. (2008) "Mitogenic effect contributes to increased virulence of *Streptococcus suis* sequence type 7 to cause *Streptococcal* toxic shock-like syndrome" Clinical and Experimental Biology 153:385-391.
Marks et al. (2012) "High levels of genetic recombination during nasopharyngeal carriage and biofilm formation in *Streptococcus pneumoniae*" mBio 3(5): e00200-12.
Short et al. (2012) "Increased Nasopharyngeal Bacterial Titers and Local Inflammation Facilitate Transmission of *Streptococcus pneumoniae*" mBio 3(5): e00255-12.
Bremell et al. (1991) "Expermental *Staphylococcus aureus* Arthritis in Mice" Infection and Immunity 59(8): 2615-2623.
Visser et al. (2005) "Proinflammatory Bacterial Peptidoglycan as a Cofactor for the Development of Central Nervous System Autoimmune Disease" The Journal of Immunology 174: 808-816.
Dominguez-Punaro et al. (2012) "*Streptococcus suis* Serotype 2, an Important Swine and Human Pathogen, Induces Strong Systemic and Cerebral Inflammatory Responses in a Mouse Model of Infection" The Journal of Immunology 179:1842-1854.
Gottschalk et al. (1991) "Characterization of Six New Capsular Types (23 through 28) of *Streptococcus suis*" Journal of Clinical Microbiology 29(11):2590-2594.

(Continued)

Primary Examiner — Albert Navarro
(74) Attorney, Agent, or Firm — Westman, Champlin & Koehler, P.A.; Z. Peter Sawicki; Visala Goswitz (57) ABSTRACT The present disclosure relates to methods and compositions administered to the lymphatic tissue of an animal to prevent or reduce the incidence of disease or disease symptoms caused by one or more disease causing entities. Tonsillar compositions can be administered to the lymphatic tissue in the oral/nasal region of the animal and can include avian antibodies from eggs of hens inoculated with one or more target disease causing entities. Treating the lymphatic tissue in the oral/nasal region with the compositions described herein can reduce or prevent the disease causing entities from adhering to the lymphatic tissue resulting in reduced infection rates. The present disclosure also relates to oral compositions that can be used to reduce or eliminate oral pathogens in animals.

20 Claims, 8 Drawing Sheets (56) References Cited

OTHER PUBLICATIONS

Capparelli et al. (2011) "The *Staphylococcus aureus* Peptidoglycan Protects Mice against the Pathogen and Eradicates Experimentally Induced Infection" PLoS ONE 6(12): e28377.

Zhou et al. (2012) "Haemophilus parasuis Encodes Two Functional Cytoethal Distending Toxins: CdlC Contains an Atypical Cholesterol Recogniton/Interaction Region" PLoS ONE 7(3): e32580.

Meijerink et al. (2012) "Immunomodulatory Effects of *Streptococcus suis* Capusule Type on Human Dendritic Cell Responses, Phagocytosis and Intracellular Survival" PLoS ONE 7(4): e35849.

Tarkowski et al. (2001) "Model systems: Modeling human *Staphylococcal* arthritis and sepsis in the mouse" TRENDS in Microbiology 9(7): 321-326.

Garmise (2007) "Novel Dry Powder Preparations of Whole Inactivated Influenza Virus for Nasal Vaccination" Dissertation; University of North Carolina at Chapel Hill.

Amass et al. (1997) "Research Update: *Streptococcus suis*" Purdue University; Departments of Veterinary Clinical Sciences, Biology, and Veterinary Pathobiology; and Swine Practitioner, Manning, Iowa.

Gottschalk et al. (1995) "*Streptococcus pneumonia* Types 19A and 19F and *Streptococcus suis* Type 8 Share Common Capsular Epitopes" Journal of Clinical Microbiology 33(9): 2492-2495.

Hamill et al. (1998) "*Streptococcus*, infection and immunity" Encyclopedia of Immunology 2217.

Olvera et al. (2010) "Virulence-associated trimeric autotransporters of Haemophilus parasuis are antigenic proteins expressed in vivo" Vet. Res. 41(26).

Aragon et al. (2010) "Invasion of endothelial cells by systemic and nasal strains of Haemophilus parasuis" Vet. J. 186 (2): 264-267; Abstract.

Akita (1993) "Chicken Egg Yolk Immunoglobulin Y and Fragments: Purification, Allergenicity and their Neutralization of *Escherichia coli* Heat Labile Toxin" Thesis; The University of British Columbia; Department of Food Science.

Kuboniwa et al. (2009) "Distinct roles of long/short fimbriae and gingipains in homotypic biofilm development by Porphyromonas gingivalis" BMC Microbiology 9:105.

Bajaj et al. (2012) "Linkage of gut microbiome with cognition in hepatic encephalopathy" Am J Physiol Gastroinfest Liver Physiol 302: G168-175.

Henao-Mejia et al. (2012) "Inflammasome-mediated dysbiosis regulates progression of NAFLD and obesity" Nature 482: 179-186.

Bagaitkar et al. (2010) "Tobacco Upregulates P. gingivalis Fimbrial Proteins Which Induce TLR2 Hyposensitivity" PLoS ONE 5(5): 39323.

Hayashi et al. (2010) "Pathogen-induced inflammation at sites distant from oral infection: bacterial persistence and induction of cell-specific innate immune inflammatory pathways" Mol Oral Microbiol 25(5): 305-316.

Njoroge et al. (1997) "A Role for Fimbriae in Porphyromonas gingivalis Invasion of Oral Epithelial Cells" Infection and Immunity 65(5): 1980-1984.

Makiura et al. (2008) "Relationship of Porphyromonas gingivalis with glycemic level in patients with type 2 diabetes following periodontal treatment" Oral Microbiol Immunol 23: 348-351.

Cunningham et al. (1996) "Helicobacter pylori and porphyromonas gingivalis Lipopolysaccharides Are Poorly Transferred to Recombinant Soluble CD14" Infection and Immunity 64(9): 3601-3608.

Ogrendis et al. (2005) "Serum Antibodies to Oral Anaerobic Bacteria in Patients with Rheumatoid Arthritis" Medscape General medicine 7(2): 2.

Noiri et al. (2004) "Localization of Porphyromonas gingivalis-carrying Fimbriae in situ in Human Periodontal Pockets" J Dent Res 83(12): 941-945.

Yu et al. 92008) "The Interleukin-17 Receptor Plays a Gender-Dependent Role in Host Protection against Porphyromonas gingivalis-induced Periodontal Bone Loss" Infection and Immunity 76(9):4206-4213.

Lamont et al. 91998) "Life Below the Gum Line: Pathogenic Mechanisms of Porphyromonas gingivalis" Microbiol. Mol. Bio. Rev. 62(4): 1244-1263.

Hajishengallis et al. (2005) "Peptide Mapping of Bacterial Fimbrial Epitopes Interacting with Pattern Recognition Receptors" Journal of Biological Chemistry 280(47): 38902-38913.

Tompkins et al. (1997) "Detection and comparison of specific human binding by Porphyromonas gingivalis and Prevotella intermedia" J. Bacteriol. 179(3): 620-626.

Moelants et al. (2011) "Detection and quantification of Citrullinated Chemokines" PLoS ONE 6(12): e28976.

Wegner et al. (2010): "Peptidylarginine deiminase from Porphyromonas gingivalis citrullinates human fibrinogen and α-enolase: Implicaitons for automimmunity in rheumatoid arthrits" Arthritis Rheum 62(9): 2662-2672.

Hayashi et al. (2010) "Pathogen-induced inflammation at sites distant from oral infection: bacterial persistence and induction cell-specific innate immune inflammatory pathways" Mol Oral Microbiol 25(5): 305-316.

Wissalink et al. (2002) "Muitiplex PCR Assays for Simultaneous Detection of Six Major Serotypes and Two Virulence-Associated Phenotypes of *Streptococcus suis* in Tonsillar Specimens from Pigs" Journal of Clinical Microbiology 40 (6): 2922-2929.

Wang et al. (2012) "Transcription analysis on response of porcine alveolar macrophages to Haemophilus parasuis" BMC Genomics 13: 68.

Madhour et al. (2011) "Cell surface proteins in S. pneumoniae, S. mitis and S. oralis" Iranian Journal of Microbiology 3 (2) 58-67.

Nilsson et al. (2007) "More than 10 years' continuous oral treatment with a specific immunoglobulin Y for the prevention of Pseudomonas aeruginosa infections: a case report" J Med Food 10(2) 375-378; Abstract.

Segura et al. (2002) "*Streptococcus suis* Interactions with Murine Macrophage Cell Line J774: Adhesion and Cytotoxicity" Infection and Immunity 70(8): 4312-4322.

Tan et al. (2008) "The key virulence-associated genes of *Streptococcus suis* type 2 are upregulated and differentially expressed in vivo" FEMS Microbiol Lett 278(1): 108-114; Abstract.

Yokoyama K. et al. "Activity of anti-Porphyromonas gingivalis egg yolk antibody against gingipains in vitro". Oral Microbiol Immunol, Oct. 2007; 22(5): pp. 352-355; abstract.

Search Report for PCT/US2014/027868, mailed Aug. 7, 2014.

Written Opinion for PCT/US2014/027688, mailed Aug. 7, 2014.

Nilsson et al. (2008) "Good effect of IgY against Pseudomonas aeruginosa infections in cystic fibrosis patients" Pediatr Pulmonol 43(9) Abstract.

Kolberg et al. (2003) "Oral administration of specific yolk antibodies (IgY) may prevent Pseudomonas aeruginosa infections in patients with cystic fibrosis: a phase 1 study" Pediatr Pulmonol 35(6) Abstract.

Rahimi, S. et al. (2007) "The effect of egg-derivd antibody on prevention of avian influenza subtype H9N2 in layer chicken" International Journal of Poultry Science, vol. 6, No. 3, p. 207-210.

Partial Supplementary European Search Report for related European patent application No. 14763054.5 dated Jul. 18, 2016.

\* cited by examiner

METHODS AND COMPOSITIONS FOR REDUCING MICROORGANISMS IN THE OROPHARYNX, NASOPHARYNX AND ORAL CAVITIES

CROSS-REFERENCE TO RELATED APPLICATION

The present application is based on and claims the benefit of U.S. provisional patent application Ser. No. 61/788,513, filed on Mar. 15, 2013, the content of which is hereby incorporated by reference in its entirety.

FIELD

The present disclosure relates to delivery of agents to oral and pharyngeal regions and particularly to reducing pathogenic microorganisms and their effects in animals through agents delivered to lymphatic tissue and to the oral cavity.

BACKGROUND

The lymphatic system is a part of the immune system and protects the body against infection and invasion by foreign organisms. The lymphatic system consists of lymphatic vessels and lymphatic tissue. Lymphatic vessels are a network of thin tubes that branch, like blood vessels, into tissues through the body. In mammals, most tissues and organs are drained by the lymphatic system. Lymphoid tissue is found in many organs, particularly the lymph nodes. Lymphoid tissues contain lymphocytes, but they also contain other types of immune cells such as macrophages, dendritic cells and eosinophils. Lymphoid tissue associated with the lymphatic system is concerned with immune functions in defending the body against infections and spread of tumors.

The lymphoid tissue may be primary, secondary, or tertiary depending upon the stage of lymphocyte development and maturation associated with the tissue. The central or primary lymphoid organs such as bone marrow generate lymphocytes from immature progenitor cells. Secondary or peripheral lymphoid organs maintain mature naive lymphocytes and initiate an adaptive immune response. The peripheral lymphoid organs are the sites of lymphocyte activation by antigen. Activation leads to clonal expansion and affinity maturation. Mature lymphocytes recirculate between the blood and the peripheral lymphoid organs until they encounter their specific antigen. Secondary lymphoid tissue provides the environment for the foreign or altered native molecules (antigens) to interact with the lymphocytes. It is exemplified by the lymph nodes, and the lymphoid follicles in tonsils, Peyer's patches, spleen, adenoids, skin, etc. that are associated with the mucosa-associated lymphoid tissue (MALT). Tonsils are collections of lymphoid tissue facing into the aerodigestive tract, i.e. the oropharynx and the nasopharynx. The set of lymphatic tissue known as Waldeyer's tonsillar ring includes the adenoid tonsil, two tubal tonsils, two palatine tonsils, and the lingual tonsil. When used unqualified, the term "tonsils" most commonly refers specifically to the palatine tonsils, which are masses of lymphatic material situated at either side at the back of the human throat. "Tonsils" as used herein refers to tonsils within the Waldeyer's tonsillar ring and includes pharyngeal tonsils, tubal tonsils, palatine tonsils and/or lingual tonsils.

Pathogenic organisms such as Staphylococci, Streptococci, *Haemophilus* are common organisms in all animals including people. *Streptococcus suis* (*S. suis*), for example, is a gram-positive bacteria. It is an increasingly important pathogen affecting the swine industry worldwide and can reside as a commensal in the upper respiratory tract of pigs. *S. suis* can be shed from sows through bodily fluids such as vaginal secretions There are many serotypes of *S. suis* and they can vary in their pathogenicity. Different types *S. suis* predominate in different countries with type 2 being the most common. Newborn piglets may become colonized with *S. suis* via vertical transmission during farrowing and suckling. Previous studies have found that *S. suis* is frequently isolated from the tonsillar area of piglets before and after weaning. Infectious *S. suis* can spread to other animals during the production stage, or cause disease due to stress at weaning.

Decreased performance and mortality resulting from *S. suis* infection have a significant economic impact on swine production. Streptococcal infections are usually characterized by variety of conditions including meningitis, septicemia, polyserisitis, arthritis, bronchopneumonia and endocarditis. The incidence of meningitis and other conditions related to streptococcal infections may be prevented by decreasing stocking density, minimizing mixing and improving ventilation and temperature control. Currently, there are no vaccines against *S. suis* infections. If disease is suspected or identified, medications such as phenoxymethyl penicillin, tetracyclines, synthetic penicillins or other antibiotics may be administered. These methods are expensive and widespread use of these can lead to resistant strains. The timing of administration of these medications can also be critical and are generally applied only when the disease levels on the farm are high. Attempts to eradicate the tonsillar carrier state of *S. suis* in early-weaned pigs with a number of antimicrobials have not been successful. Moreover, new serotypes are being isolated each year.

There is growing concern about the impact of *S. suis* as a zoonotic agent, particularly for individuals who handle pigs and pig carcasses. Southeast Asian countries such as China, Thailand and Vietnam have experienced the majority of human cases. A recent US study reported that individuals exposed to swine had higher titers of antibodies to serotype 2 *S. suis*, compared with non-exposed individuals.

Periodontal diseases characterized by infection with gram-negative pathogens such as *Porphyromonas gingivalis* can induce a chronic inflammatory response. This can result in oral inflammatory bone destruction. Recent evidence suggests a role for *P. gingivalis* mediated periodontal disease as a risk factor for several systemic diseases including diabetes, stroke and atherosclerotic cardiovascular disease. Infections of the oral cavity by microorganisms such as *Candida Albicans* can occur in humans and are often side effects in individuals being treated for other conditions. Infection of the mouth and throat with *C. Albicans* in conditions such as thrush can make routine eating and swallowing extremely uncomfortable.

SUMMARY

In one aspect, the present invention relates to a method of reducing or eliminating pathogenic infections in an animal. The method includes treating lymphatic tissue in the oropharynx and the nasopharynx of the animal with a tonsillar composition to reduce or eliminate one or more disease causing entities from the lymphatic tissue, wherein the tonsillar composition comprises avian antibodies from eggs of hens inoculated with one or more of the disease causing entities and wherein the avian antibodies bind and/or neutralize the one or more disease causing entities.

In another aspect, the present invention relates to a method of reducing or eliminating one or more disease causing entities in the oral cavity of an animal. The method includes treating the oral cavity of the animal with a composition comprising avian antibodies from eggs of hens inoculated with one or more of the disease causing entities, wherein the treatment comprises contacting the oral cavity with the composition to reduce or eliminate disease causing entities from the oral cavity of the animal.

In yet another aspect, the present invention relates to a method of operating a farm comprising farm animals. The method includes providing the farm animals with a composition to reduce or eliminate disease causing entities from the lymphatic tissue of the orpharynx and/or nasopharynx. The composition comprising avian antibodies from eggs of hens inoculated with one or more of the disease causing entities, wherein the providing comprises inclusion of the composition in the drinking water of the farm animals.

In a further aspect, the present invention relates to a composition including drinking water and avian antibodies wherein the drinking water does not include a buffering system. The composition includes a tonsillar composition comprising drinking water and avian antibodies to one or more disease causing entities, wherein the drinking water does not include a buffering system and said avian antibodies are in sufficient amount to inactivate one or more of the disease causing entities in the lymphatic tissue of the oropharynx and/or nasopharynx.

In yet a further aspect, the present invention relates to an oral composition comprising a liquid and avian antibodies to one or more disease causing entities, wherein the liquid is drinking water or mouthwash, wherein the drinking water does not include a buffering system and said avian antibodies are in sufficient amount to inactivate one or more of the disease causing entities in the oral cavity.

DETAILED DESCRIPTION OF ILLUSTRATIVE EMBODIMENTS

The present disclosure includes methods and compositions administered to the lymphatic tissue of an animal to prevent or reduce the incidence of disease or disease symptoms caused by one or more disease causing entities. Tonsillar compositions can be administered to the lymphatic tissue in the oral/nasal region of the animal and can include avian antibodies from eggs of hens inoculated with one or more target disease causing entities. Treating the lymphatic tissue in the oral/nasal region with the compositions described herein can reduce or prevent the disease causing entities from adhering to the lymphatic tissue resulting in reduced infection rates. Surprisingly, the administration of the composition to the lymphatic tissue can also generate a systemic effect by reducing the symptoms associated with an infection of the disease causing entities. The present disclosure also includes oral compositions that can be used to reduce or eliminate oral pathogens in animals.

"Composition" as used herein refers to tonsillar compositions and/or oral compositions. "Oral/tonsillar composition" as used herein refers to oral compositions and tonsillar compositions.

"Lymphoid" and "lymphatic" as referred to herein are equivalent and are used interchangeably in the present disclosure.

"Avian antibodies" as used herein can refer to and include purified avian antibodies, partially purified avian antibodies or complete egg contents that include the avian antibodies.

"Egg powder" as referred to herein relates to spray dried egg contents.

"Disease causing entities" as used herein relates to pathogenic microorganisms and material derived from these pathogenic microorganisms. Disease causing entities can include microbial cells, cellular components and/or cellular products. These cellular components and/or products may include enterotoxins, endotoxins, exotoxins, leukotoxins, peptidoglycan, capsular polysaccharide or other such entities. The pathogenic organisms can include bacteria, viruses, yeast, parasites, fungi and other infectious agents.

The compositions of the present disclosure can include antibodies, preferably avian antibodies, produced to bind and/or neutralize one or more disease-causing entities. The compositions generally include avian antibodies from eggs of hens inoculated with one or more disease causing entities. The avian antibodies can be against the one or more disease causing entities. The avian antibodies can bind and prevent the disease causing entities from entering into the lymphatic system. Disease causing entities interact with the immune cells in the lymphatic tissue leading to entry of the disease causing entities into the lymphatic system and the blood stream as well as other serous fluids of the body. This can lead to systemic complications that include septicemia, arthritic conditions, meningitis and other blood/serous conditions in an animal. The disease causing entities can be bound and removed by delivering the avian antibodies to the oral/nasal lymphoid tissues and thus decreasing the incidence of entry into the lymphatic system.

The compositions that include the avian antibodies can be formulated for administration in drinking water. In some embodiments, the drinking water may not include any added salts that act as a buffering system. Salts may be present in the avian antibody preparation. Any salt that may be present in the avian antibody preparation is diluted when the avian antibody is added to the drinking water and generally is not sufficient or capable of acting as a buffer. Tonsillar compositions including the avian antibodies can be formulated in a liquid for application to the lymphoid tissue of the oropharynx and/or the nasopharynx region. In some preferred embodiments, the tonsillar composition includes drinking water and the avian antibodies. Preferably, the tonsillar composition including the avian antibodies and drinking water does not include an added buffering system such as a PBS buffering system.

Compositions including the avian antibodies can be formulated into an oral composition for application to the oral cavity. In some oral composition embodiments, the avian antibodies are formulated in drinking water. Preferably, the oral composition including avian antibodies and drinking water does not include an added buffering system such as a PBS buffering system. Oral compositions with the avian antibodies may also be formulated in a mouthwash. The mouthwash may be commercially available mouthwash that is, for example, available in drugstores. Preferably, the mouthwash has little to no alcohol. Commercially available mouthwashes such as ACT, Colgate and Hello may be used. Oral compositions may be used to gargle or rinse the oral cavity to reduce or eliminate the disease causing entities related to, for example, periodontal disease in the oral cavity. Oral compositions are generally expelled from the oral cavity after the rinse or gargle.

The present invention also includes methods for reducing or eliminating one or more disease causing entities in the oropharynx, nasopharynx and/or the oral cavity of the animal. The method includes application of the compositions described herein to the oral/nasal region of an animal. In some embodiments, tonsillar compositions are delivered to the lymphoid tissue in the oro- and nasopharynx region, preferably through drinking water. Providing the tonsillar compositions through drinking water can be advantageous for large-scale delivery of antibodies to a number of animals at one time. This eliminates the need to deliver the compositions individually to each animal. Without being bound to any specific theory, application of the tonsillar composition to the lymphoid tissue can bind and inactivate the disease causing entities in the lymphoid tissue. Surprisingly, the inactivation can be sufficient to decrease the systemic effects generally associated with infections from the target disease causing entities such as *S. suis*. Compositions targeted against *S. suis*, for example, can reduce or eliminate the occurrence of meningitis, arthritis, endocarditis and other symptoms associated with a *S. suis* infection in pigs.

In some embodiments, the method includes delivery of oral compositions to the oral cavity by rinsing and/or gargling. The oral compositions, for example, can be provided as a mouthwash or rinse. These oral compositions can be effective for reducing disease causing entities related to periodontal disease and/or to other undesirable microorganisms present in the oral cavity. These compositions can be advantageous against periodontal disease causing organisms that can result in systemic effects as increased risks of atherosclerosis, diabetes, stroke and the like.

The compositions described herein include avian antibodies against one or more disease causing entities. Disease causing entities can include a variety of microorganisms and/or cellular components or products derived from these microorganisms. Microorganisms can be bacteria, viruses, yeast, parasites, fungi and the like. Examples of microorganisms used to produce the antibodies include, for example, microorganisms from *Staphylococcus, Streptococcus, Haemophilus, Aerococcus, Candida* and *Porphrymonas*. The bacterial microorganisms can be gram-positive bacteria or gram-negative bacteria. In some embodiments, the microorganisms are *Staphylococcus hyicus, Staphylococcus aureus, Staphylococcus scuri, Streptococcus pneumoniae, Streptococcus suis, Streptococcus iniae, Streptococcus agalactiae, Streptococcus pyogenes, Haemophilus parasuis, Aerococcus viridans, Treponema denticola, Bulleria extructa*, and the like. In other embodiments, microorganisms can include *Porphrymonas gingivalis, Prevotella intermedia, Actinobacillus actinomycetemcomitans, Bacteriodes forsythus, Candida albicans, Heliobacter pylori, Pseudomonas aeruginosa* and the like. Disease causing entities can also be viruses and can include, for example, Porcine Reproductive and Respiratory virus (PRRSv), Influenza virus, Porcine CircoVirus, Porcine Epidemic Diarrhea virus (PEDv), and Herpes virus.

The compositions described herein include avian antibodies. Compositions that include non-avian antibodies are also contemplated and are within the scope of this disclosure. Compositions can be spray-dried, powdered compositions. Alternatively, the compositions can be liquid compositions comprising the avian antibodies. The liquid compositions generally are suspensions or solutions derived from the addition of spray-dried powder to water or other liquids. The antibodies included in the compositions can be purified antibodies, partially purified antibodies or unpurified antibodies, i.e. complete egg contents. Avian antibodies can be raised against any of the one or more disease causing entities by using the disease causing entities as antigens or immunogens in hens. Hens are inoculated with one or more disease causing entities. The eggs from the inoculated hens are then collected. Methods for inoculating hens with the desired immunogens are described, for example, in U.S. Patent Publication No. US2011/0274701 to Mitteness et al. and incorporated herein by reference.

Generally, the contents of the collected eggs from hens inoculated with the one or more disease causing entities are separated from the egg shells. In some embodiments, the antibodies are purified or partially purified from the egg contents before inclusion or use in a composition. In yet other embodiments, the egg yolks may be separated from the egg whites and incorporated into the compositions. In some preferred embodiments, the avian antibodies are unpurified egg contents and the compositions thus include complete egg contents.

In some exemplary embodiments, the avian antibodies, for example, can be egg contents, spray dried to a powder and stored for long term usage. Stabilizers such as trehalose may be included to the avian antibodies prior to or after drying. The avian antibodies from hens inoculated with one specific target antigen, i.e. one disease causing entity, may be pooled and dried for storage.

Compositions can include antibodies against one disease causing entity and are referred to herein as monovalent compositions. Alternatively, avian antibodies from hens inoculated with different target antigens may be pooled prior to drying or after drying. Preferably, each hen is inoculated with only one target antigen. Avian antibodies derived from hens inoculated with one target antigen can be mixed with avian antibodies derived from hens inoculated with other target antigens resulting in compositions having antibodies specific for binding two or more different target antigens or disease causing entities. Compositions formulated using a mixture of avian antibodies are referred to as multivalent compositions. A quadravalent composition, for example, has antibodies against four different antigens.

The avian antibodies, if dried, may be used directly or as an additive to liquids. Prior to use, dried avian antibodies may be resuspended in a liquid, for example, a PBS buffer, water and the like. In some embodiments, the dried avian antibodies may be added to a mouthwash or rinse. The mouthwash or rinse can be from commercial sources such as found in drug stores.

The compositions of the present disclosure include resuspended avian antibodies. The composition can be a suspension of the avian antibodies or a solution containing dissolved avian antibodies. The composition can be used as a stock solution and further diluted into water, buffer or other liquids. The composition can, for example, can be used as stock solution and added at a desired concentration and rate to drinking water of the animals. The composition may be added to a mouthwash.

In some embodiments, the compositions are formulated into a tonsillar composition. In other embodiments, the compositions are formulated into an oral composition. The tonsillar composition can include antibodies against one or more disease causing entities that may be present in the lymphatic tissue of the oropharynx and the nasopharynx. Preferably, the tonsillar composition includes avian antibodies against one or more disease causing entities that can be present or can colonize in the lymphatic tissue or the oropharynx and the nasopharynx. The oral compositions can include antibodies against one or more disease causing entities that can be present or can colonize in the oral cavity of the animal.

Additional components may be included in the compositions described herein to stabilize the composition or to enhance the activity of the composition. The components can include, for example, sugars such as trehalose that stabilize the antibodies in the composition. The components can also include preservatives. The composition may include potassium sorbate, citric acid, EDTA and the like.

In one exemplary embodiment, hens are inoculated with *S. suis* and/or cellular components of *S. suis*. The avian antibodies from eggs collected from these hens can be used to formulate tonsillar compositions. The amount of the avian antibody in the tonsillar composition can vary. In one exemplary embodiment, nursery pigs are provided with tonsillar compositions having spray dried egg contents (egg powder) as the source of the avian antibodies in drinking water. The amount of egg powder delivered may be at least about 0.25 g of egg powder/head/day, preferably between about 0.5 g/head/day and about 1.5 g/head/day of egg powder and more preferably, about 0.75 g of egg powder/head/day. Amounts of egg powder outside of this range are also within the scope of this invention.

The percentage of a specific avian antibody (antibody specifically against one target disease causing entity) in the total antibody component of the composition can vary. Spray dried egg powder can include about 4 mg of antibody per gram of egg powder. Antibody contents outside of this range are also suitable. A monovalent composition preferably has about 100 percent of the antibody present in the composition against the target antigen. In multivalent compositions, the percentage of a specific antibody in the total antibody component is, preferably at least about 10 percent of the total antibody present in the composition. For example, if egg powder is used as the source of the avian antibody and the target disease causing entity is *S. suis* serotype 2, then preferably at least about 10 percent of the egg powder used in the composition is derived from eggs of hens inoculated with *S. suis* serotype 2. In a quadravalent composition, for example, egg powders against each of four target antigens provide about 25 percent of the egg powder. Compositions with greater percentages of specific antibody against the target disease causing entity are suitable and all are within the scope of the invention.

The compositions can be used in a variety of animals such as swine, bovine, human and the like. In one exemplary embodiment, the tonsillar composition is used in swine. The tonsillar composition may also be used in humans. In one exemplary embodiment, the oral composition can be provided to humans.

The amount of avian antibody in the oral composition can vary. In embodiments using egg powder, the amount of egg powder in a 4 ounces of liquid can be, for example be at least about 0.1 grams of egg powder. Preferably, the amount of egg powder is between 1.0 grams of egg powder and about 8 grams egg powder. In one exemplary embodiment, about 4.5 grams (about 1 teaspoon) of egg powder was added to 4 ounces of drinking water. Amounts of egg powder outside of this range are within the scope of this invention.

The present disclosure includes methods for reducing or eliminating the disease causing entities from the microbial flora of the lymphoid tissue. The method can include applying the compositions described herein to the lymphatic tissue in the oropharynx and nasopharynx of the animal. In exemplary embodiments, the tonsillar composition is formulated as a concentrated composition or stock solution and delivered into drinking water through the water lines using a commercial proportioner of the animals at a desired concentration.

Compositions with avian antibodies formulated in drinking water are preferably prepared within two days prior to administration, more preferably prepared within twenty-four hours prior to administration.

In one exemplary tonsillar composition embodiment, the desired amount of spray dried egg powder is placed in a bucket or chemical proportioner and sufficient drinking water is added to solubilize the egg powder to create a stock solution. This stock solution is proportioned into the drinking water of the animals, for example, using a commercial proportioner at a rate calibrated for delivery of all the egg powder in a twenty-hour cycle. Thus, the desired amount of egg powder is administered to the animals throughout the twenty-four hour period whenever the animals ingest drinking water. Preferably, a new stock solution is made each day.

The amount of avian antibody administered to the animal can vary. In one exemplary embodiment, a multivalent composition including multiple antibodies was provided to pigs. The multivalent composition included, for example, egg powder containing the avian antibodies against *S. suis* type 1, *S. suis* type 2, *Pasteurella multocida*, *Actinobacillus suis*, *S. aureus*, *S. hyicus*, *Mycoplasma hyopneumonia*, and *Haemophilus parasuis*. Nursery pigs can be provided the multivalent composition at an amount of at least about 0.25 grams/head in about 24 hours. Preferably the range of powder provided was between about 0.30 g/head to about 3.0 g/head in 24 hours, more preferably between about 0.5 g/head and about 1.5 g/head in 24 hours and even more preferably about 0.75 g/head in about 24 hours. Preferably, the amount of specific antibody against each target antigen included in the composition was at least about 10 percent of the total antibody present in the composition.

The animals may be treated with the compositions for a varying amount of time. The animals may be treated with the tonsillar compositions for at least 5 days, preferably at least 10 days and more preferably at least 14 days. The composition may be administered to the lymphoid tissue in a variety of ways. Generally, the tonsillar compositions can be provided by localized delivery to lymphatic tissue, preferably the Waldeyer's tonsillar ring and the surrounding MALT. The composition may be provided in the drinking water of the animal. Addition of the tonsillar composition to the drinking water by use of, for example, a chemical proportioner provides the avian antibodies to the animal throughout the day. The stability of the avian antibodies is advantageous for use in this method of delivery. The composition may also be sprayed onto the lymphoid tissue, injected into the lymphoid tissue of the oropharynx and/or nasopharynx to reduce or eliminate the number of disease causing entities. Other methods of providing the composition onto the lymphoid tissue of the oral/nasal regions may be used and are within the scope of this invention.

Treatment with the oral compositions can be for at least one day, preferably at least 2 days and more preferably at least 3 days. Oral compositions may be used at least once a day, preferably 2-3 times a day. Oral cavity is generally rinsed with the oral composition for at least about one-minute, preferably for at least about two to three minutes. The oral composition is usually not ingested. A volume of oral composition can be placed in the oral cavity and rinsed and gargled for the desired amount of time and then removed.

After the symptoms from infection with the disease causing entity have been alleviated, a maintenance regimen may be provided to the animal to eliminate or maintain the low level of disease causing entity. Maintenance regimens can also keep the target microorganisms from propagating in the animal and/or reinfecting the animal. The maintenance regimen may include less frequent or less intensive use of the compositions. The compositions, for example, may be used two or three times a week instead of daily use that may be beneficial during a full blown infection. Maintenance regimens can be provided for tonsillar and oral composition applications.

The present invention also includes methods of reducing or eliminating the symptoms or conditions resulting from infections of the disease causing entities. These conditions include, for example, septicemia, arthritic conditions, meningitis and other blood/serous conditions as a result of pathogenic infections from disease causing entities in the oropharynx and/or nasopharynx of an animal. Generally, elimination or reduction of symptoms related to arthritis, joint swelling and other symptoms that are characteristic of the pathogenic infection can be seen after administration of the tonsillar composition for a sufficient period of time as described herein. Reduction of oral disease symptoms such as periodontal disease, thrush, bad breath and other symptoms related to the presence of undesirable microorganisms can be seen after administration of oral compositions for a sufficient period of time as described herein.

The present disclosure also includes methods of operating a farm with animals. The method includes providing the compositions described herein to the animals. In some embodiments, the tonsillar compositions are included in the drinking water as described herein. The tonsillar compositions may be administered at the first evidence of a pathogenic infection. Alternatively, the tonsillar compositions may be administered before evidence of a pathogenic infection. The tonsillar compositions may be provided for preventative or therapeutic purposes. The tonsillar compositions are provided through a commercial proportioner that continuously maintains a desired concentration of the avian antibodies in the drinking water. The animals are provided the antibodies every time they drink the water.

EXAMPLES

Example 1—Long-Term Production of Antibodies

This example demonstrates that hens inoculated with the antigen can produce avian antibodies with binding specificity over a long period. Eggs were collected from hens and the contents separated from the shells. The egg contents were water extracted for egg protein according to the method of Akita et al. and incorporated herein by reference. ELISA test(s) were performed to demonstrate the antibody binding of the homologous antibody-antigen complexes for each microorganism. By homologous it is meant that the antibodies present were from the egg contents of hens inoculated with the target antigen. They represent the satisfactory production of such antibodies within the hen(s) over a time course of several months.

The test was set up with a calculated 1 mg/ml bacterial antigen. This was then tested against a dilution scheme of the specific or homologous antibody. The dilution of the water extracted egg protein containing the antibody ranged from the greatest concentration (1:600) to the least concentration (1:38,400). Absorbance at 450 nm was measured. Any data point over 0.5 was considered to be significant.

Table 1 below shows the absorbance for the indicated dilutions of antibodies obtained from eggs collected from hens after the specified period of time from inoculation. Table 1 shows the results for the antibodies raised against *C. albicans*. Tables 2, 3 and 4 show similar data for *B. extructa, P. gingivalis*, and *T. denticola*, respectively. Stability tests for antibodies against *P. gingivalis* were carried out for 9 months. FIGS. 1-4 illustrate the data from Tables 1-4 in a bar graph.

TABLE 1

| | | | |
|---|---|---|---|
| | | *C. albicans* | |
| Dilution | Initial | 3 month | 6 month |
| 1:600 | 2.3735 | 2.6938 | 2.4255 |
| 1:1200 | 2.4818 | 2.5855 | 2.524 |
| 1:2400 | 2.524 | 2.7443 | 2.5453 |
| 1:4800 | 2.4293 | 2.396 | 2.3758 |
| 1:9600 | 2.1593 | 1.8805 | 2.0605 |
| 1:19200 | 1.6428 | 1.2955 | 1.4698 |
| 1:38400 | 1.1365 | 0.7458 | 0.9795 |

TABLE 2

| | | | |
|---|---|---|---|
| | | *B. Extructa* | |
| Dilution | Initial | 3 month | 6 month |
| 1:600 | 2.285 | 2.2593 | 2.0483 |
| 1:1200 | 2.343 | 2.067 | 1.9305 |
| 1:2400 | 2.3413 | 2.0625 | 1.6908 |
| 1:4800 | 2.1773 | 1.6858 | 1.401 |
| 1:9600 | 1.917 | 1.2305 | 1.0608 |
| 1:19200 | 1.565 | 0.6168 | 0.7373 |
| 1:38400 | 1.1593 | 0.2343 | 0.4895 |

TABLE 3

| | | | | |
|---|---|---|---|---|
| | | *P. gingivalis* | | |
| Dilution | Initial | 3 month | 6 month | 9 month |
| 1:600 | 2.6173 | 2.355 | 2.1203 | 2.1405 |
| 1:1200 | 2.7133 | 2.177 | 2.4838 | 1.9663 |
| 1:2400 | 2.5658 | 1.859 | 2.574 | 1.6705 |
| 1:4800 | 2.2885 | 1.5125 | 2.4885 | 1.288 |
| 1:9600 | 2.0273 | 1.0675 | 1.7713 | 0.844 |
| 1:19200 | 1.632 | 0.675 | 0.8215 | 0.5063 |
| 1:38400 | 1.174 | 0.3673 | 0.717 | 1.017 |

TABLE 4

| | T. denticola | | |
|---|---|---|---|
| Dilution | Initial | 3 month | 6 month |
| 1:600 | 2.6173 | 2.2628 | 2.1203 |
| 1:1200 | 2.7133 | 2.1553 | 2.4838 |
| 1:2400 | 2.5658 | 1.9618 | 2.574 |
| 1:4800 | 2.2885 | 1.6798 | 2.4885 |
| 1:9600 | 2.0273 | 1.3655 | 1.7713 |
| 1:19200 | 1.632 | 0.969 | 0.8215 |
| 1:38400 | 1.174 | 0.6645 | 0.717 |

These results demonstrate that hens inoculated with the antigens can produce the avian antibodies over extended periods of time. This demonstrates hens consistent response and production of suitable antibody.

Example 2—Tonsillar Composition

Unacceptable death loss among 12-14 pound pigs was seen as they were weaned from the sow and transported to the nursery facility located on another farm. Infections with *Haemophilus parasuis* and *Streptococcus suis* had been diagnosed by the producer's Veterinarian. Tests were conducted to see if the addition of an egg antibody to the drinking water would, over time, lower the numbers of these pathogens on the surface of the tonsils and thereby reducing the number of infections and nursery mortalities.

The pigs in this production flow were weaned at 18-22 days of age and were assembled into groups of approximately 1,000 animals and entered into the nursery barns where they stayed for about 8 weeks. When the pigs weighed about 60 pounds, they were removed from the nursery to populate finishing barns.

Two groups of pigs were compared from the same sow farm and identical health histories. All of the pigs were on normal protocols except that one group received about 0.75 grams/head/day of spray dried egg made from hens that had been immunized with antigens of *Streptococcus suis* and *Haemophilus parasuis*. The egg powder was delivered continually for 14 days through the water lines via a commercial proportioner that delivered a stock solution of the egg and water diluted to 1:128. The data collected was nursery mortalities and antibiotic injections required. A summary of the data collected is shown below in Table 1.

TABLE 5

| # Head | Antibody | Total Mortalities | % Mortalities | Treatments | Treatments/Pig |
|---|---|---|---|---|---|
| 993 | Yes | 33 | 3.32% | 114 | 0.11 |
| 1002 | No | 191 | 19.06% | 3,680 | 3.67 |

At the end of the two-week period the non-treated pigs appeared gaunt, rough haired and lethargic with dozens of arthritic animals in the group. In contrast, the treated pigs were smooth-haired and energetic with only 6 pigs in the sick pen exhibiting mild diarrhea. No arthritic pigs were observed. Necropsied pigs from the non-treated room exhibited the typical visible lesions of polyserositis, polyarthritis, fibrinous meningitis, pericarditis, and/or peritonitis. Tonsil tissue from 4 necropsies from the untreated pigs was cultured and in every sample *H. parasuis* and *S. suis* was recovered. Three of the treated pigs were necropsied with none of the lesions described above observed. Tonsil tissue from the treated pigs yielded no *H. parasuis* or *S. suis*.

Example 3—Stability of Antibodies in Mouthwash

Studies were performed with the monovalent homologous anti-*Porphyromonas gingivalis* antibody to study the stability of the antibody solutions when diluted into commercial mouthwash. The use of a quadravalent composition against *Candida albicans* in mouthwash was also examined in the same study. The quadravalent composition had antibodies against *C. albicans, P. gingivalis, B. extructa* and *T. denticola* The duration of antibody within such products was examined. This is a time course of approximately 3 months. The antibodies from water extracted egg protein were diluted into either a buffer or into one of four commercially available mouthwashes, ACT, Colgate, Listerine or Hello. The mouthwashes with the added antibodies were stored at room temperature and samples were removed at the indicated interval and tested for antigen binding using an ELISA test. The ELISA test was set up with a calculated 1 mg/ml bacterial antigen and the indicated dilution of the respective antibody.

Figure 1:
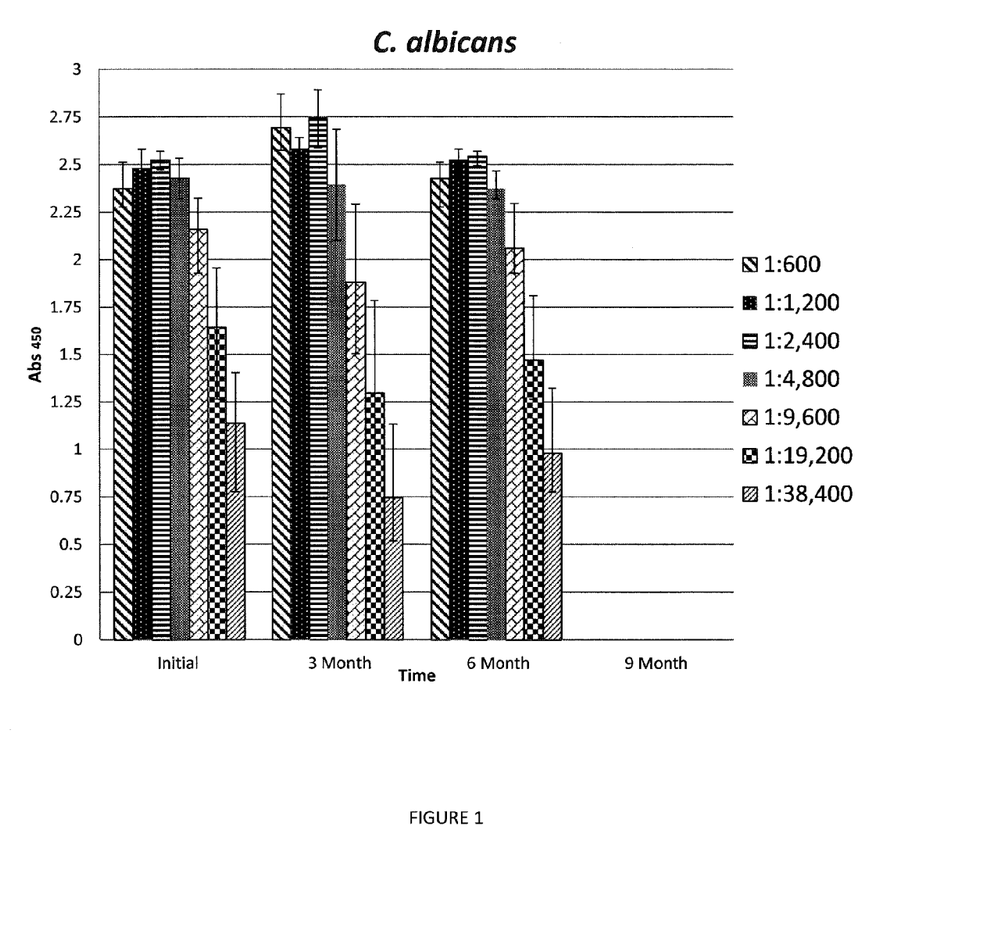
FIG. 1 is a bar graph illustrating the activity of antibodies against *C. albicans* at different concentrations from eggs collected at the indicated period.
Figure 2:
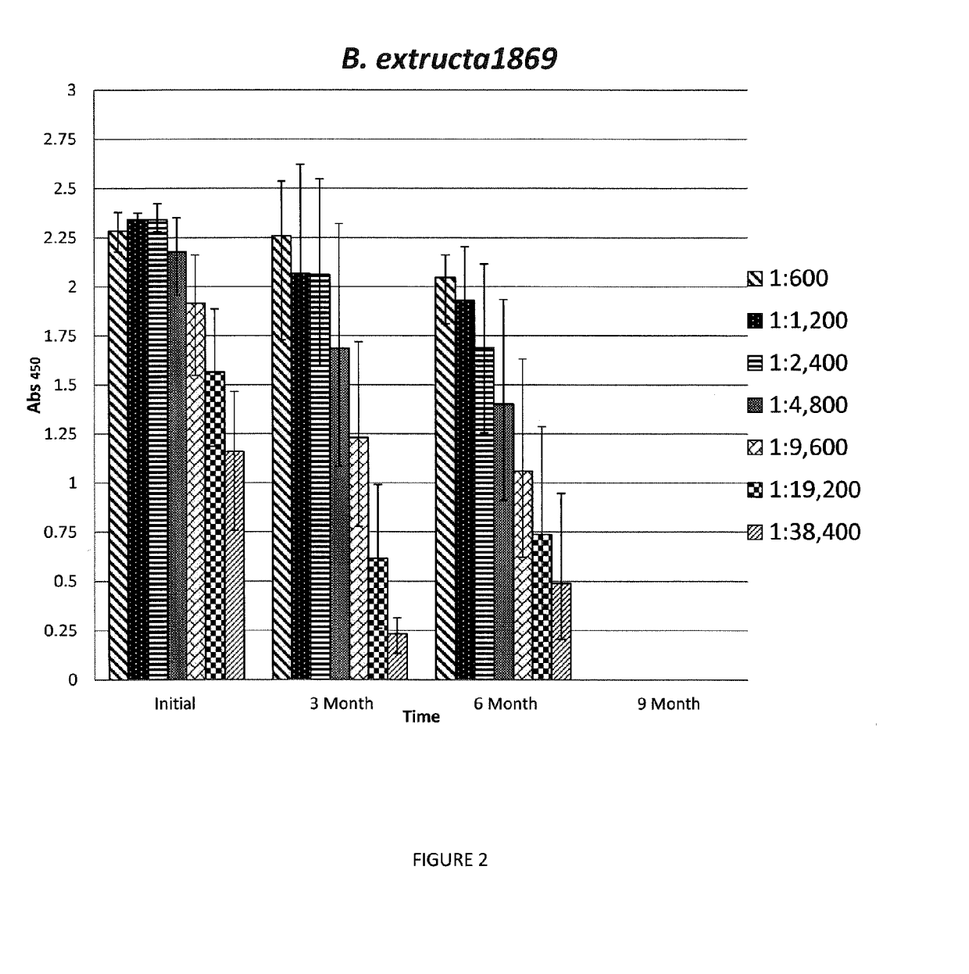
FIG. 2 is a bar graph illustrating the activity of antibodies against *B. extructa* at different concentrations from eggs collected at the indicated period.
Figure 3:
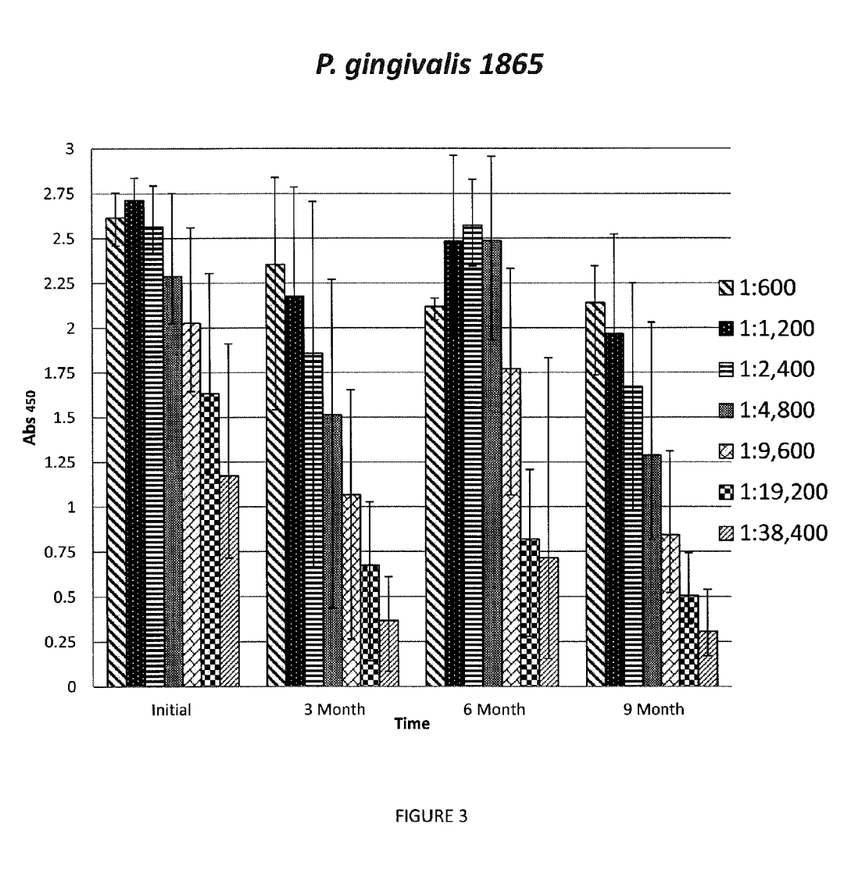
FIG. 3 is a bar graph illustrating the activity of antibodies against *P. gingivalis* at different concentrations from eggs collected at the indicated period.
Figure 4:
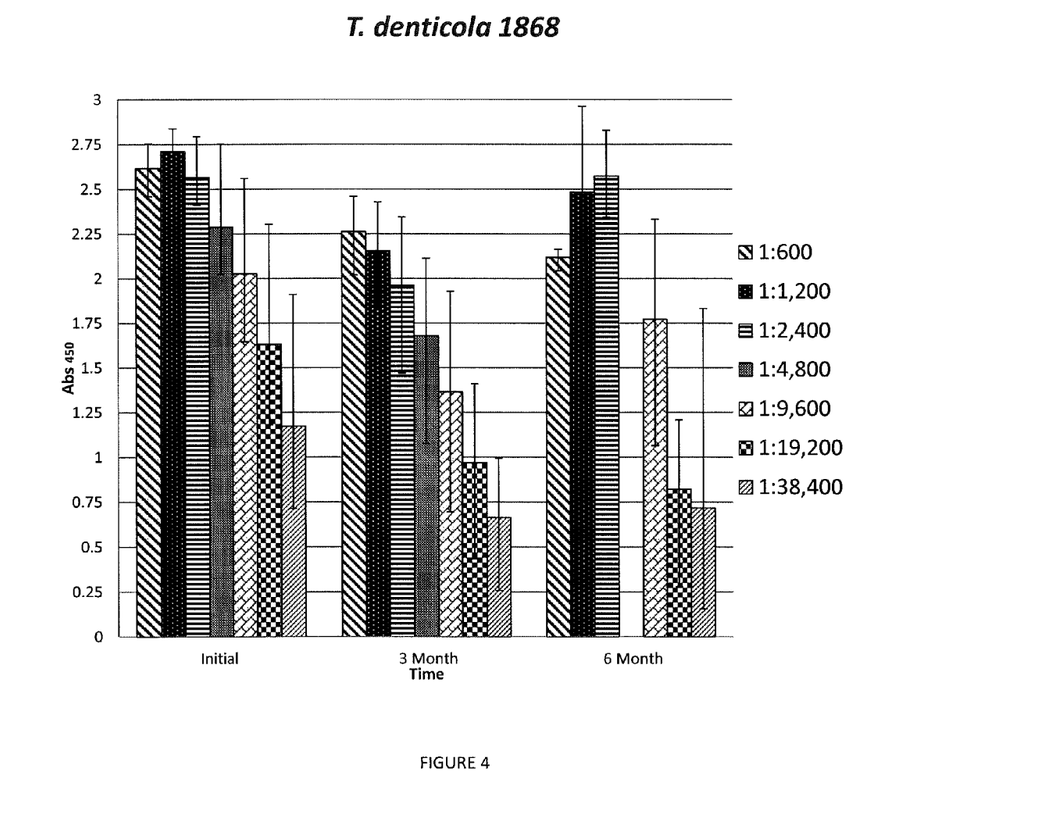
FIG. 4 is a bar graph illustrating the activity of antibodies against *T. denticola* at different concentrations from eggs collected at the indicated period.
Figure 5:
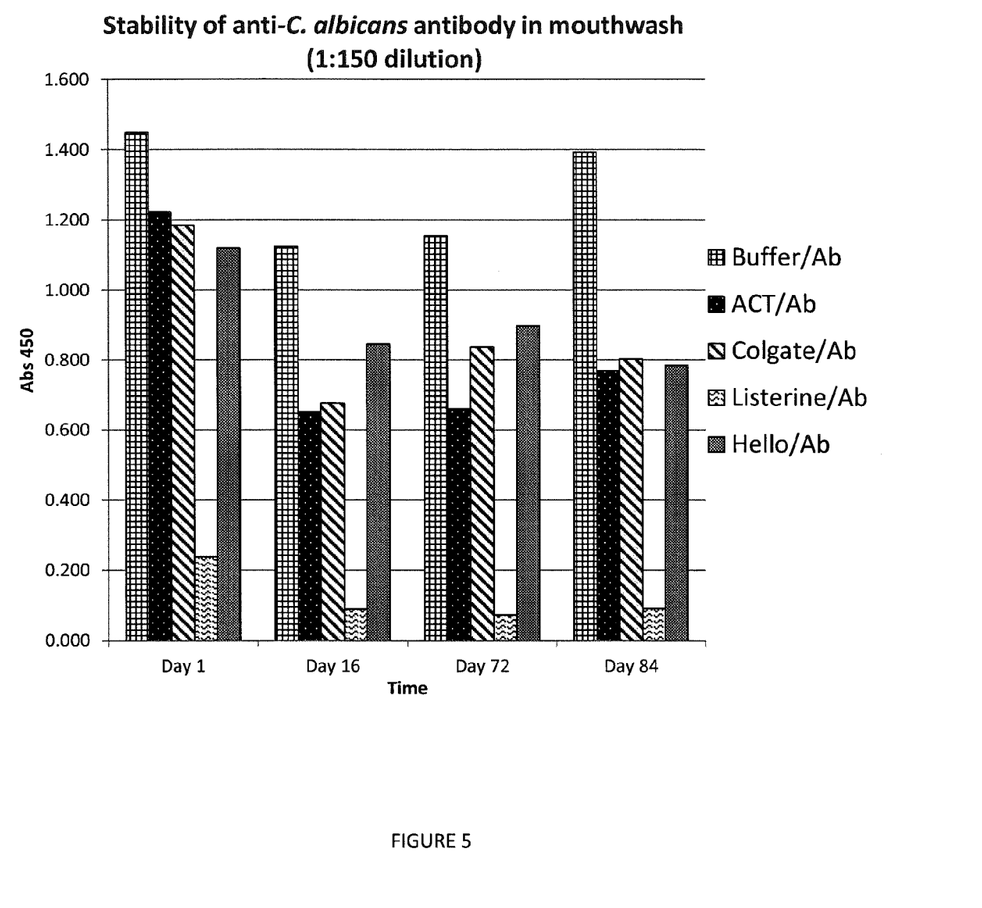
FIG. 5 is a bar graph illustrating the stability of antibodies against *C. albicans* in different mouthwashes at a 1:150 dilution over the indicated period.
Figure 6:
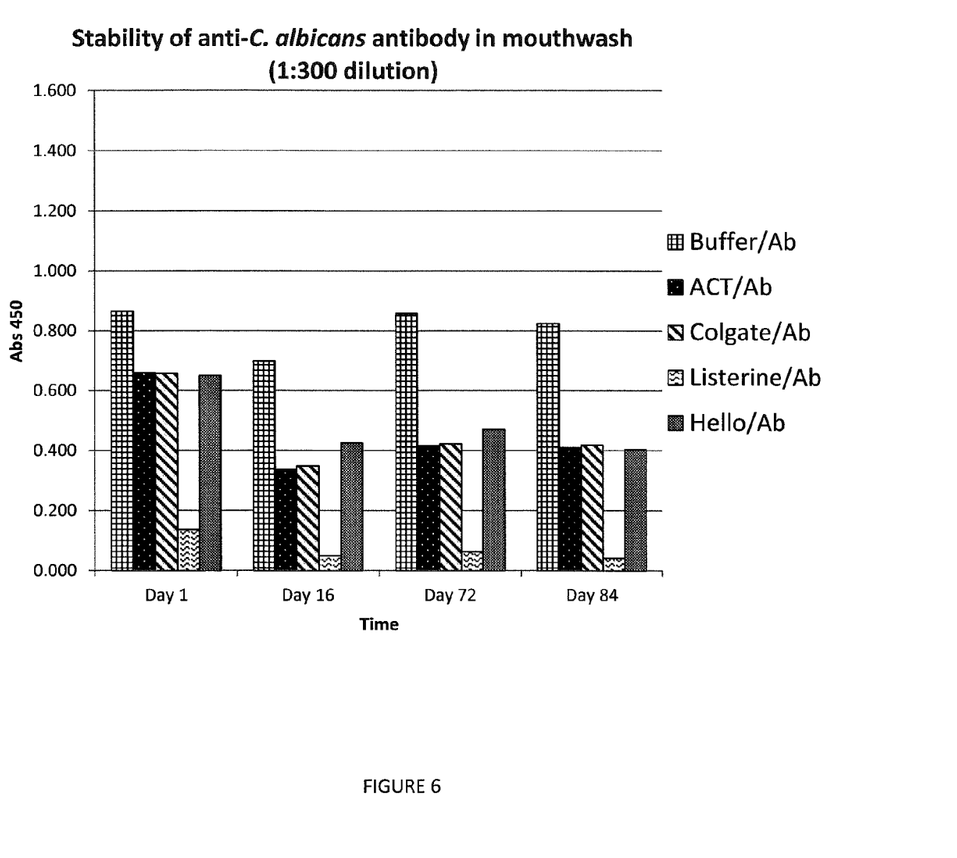
FIG. 6 is a bar graph illustrating the stability of antibodies against *C. albicans* in different mouthwashes at a 1:300 dilution over the indicated period.
Figure 7:
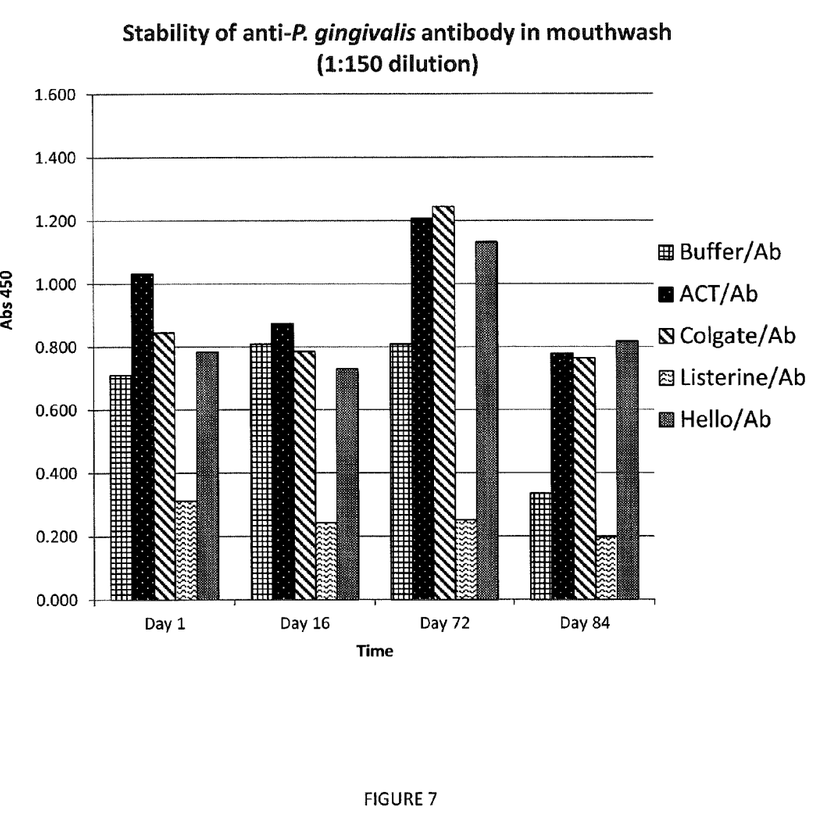
FIG. 7 is a bar graph illustrating the stability of antibodies against *P. gingivalis* in different mouthwashes at a 1:150 dilution over the indicated period.
Figure 8:
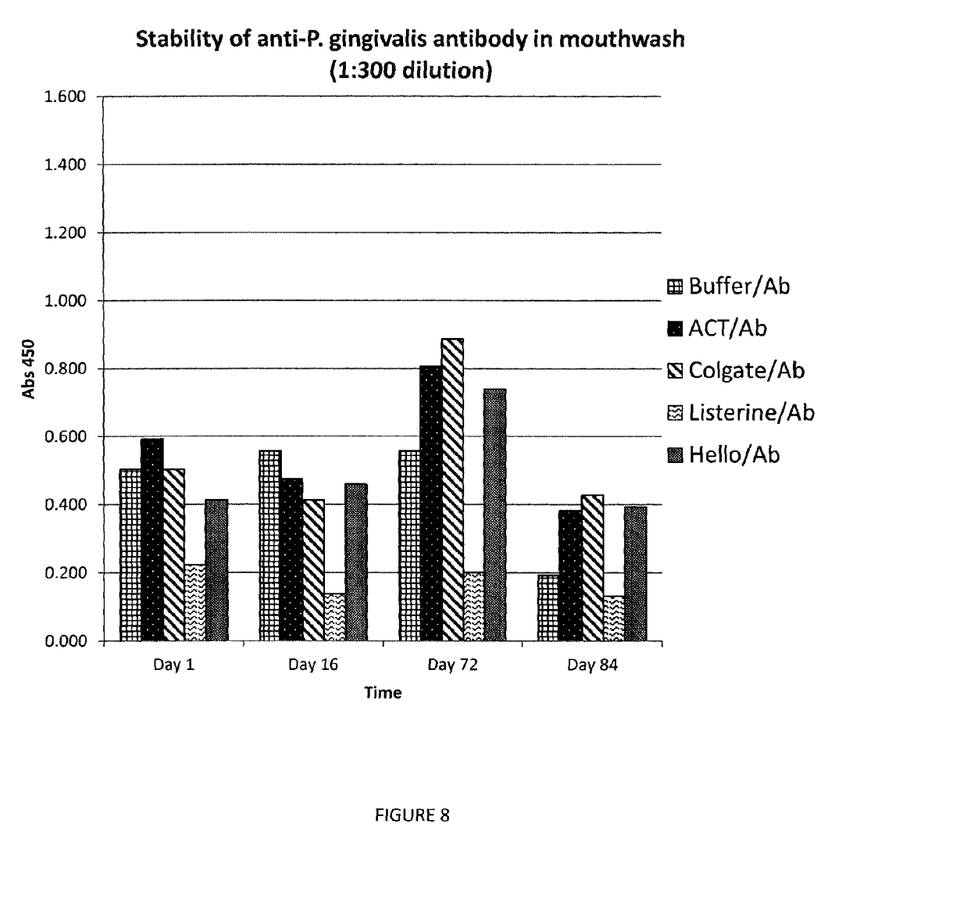
FIG. 8 is a bar graph illustrating the stability of antibodies against *P. gingivalis* in different mouthwashes at a 1:300 dilution over the indicated period.

As shown below in Table 6A-6B and Table 7A-7B, the anti-*C. albicans* antibody and the anti-*P. gingivalis* antibody are stable in ACT, Colgate and Hello mouthwashes. The antibodies were inactive in Listerine mouthwash, presumably due to the amount of alcohol content in the Listerine mouthwash. FIGS. 6-8 illustrate the results in a bar graph.

TABLE 6A

Stability of anti-*C. albicans* antibody in mouthwash (1:150 dilution)

| Mouthwash | Day 1 | Day 16 | Day 72 | Day 84 |
|---|---|---|---|---|
| Buffer/Ab | 1.449 | 1.124 | 1.155 | 1.393 |
| ACT/Ab | 1.223 | 0.652 | 0.660 | 0.769 |
| Colgate/Ab | 1.185 | 0.677 | 0.837 | 0.803 |
| Listerine/Ab | 0.238 | 0.090 | 0.073 | 0.092 |
| Hello/Ab | 1.119 | 0.846 | 0.898 | 0.785 |

TABLE 6B

Stability of anti-*C. albicans* antibody in mouthwash (1:300 dilution)

| Mouthwash | Day 1 | Day 16 | Day 72 | Day 84 |
|---|---|---|---|---|
| Buffer/Ab | 0.865 | 0.700 | 0.858 | 0.825 |
| ACT/Ab | 0.660 | 0.336 | 0.417 | 0.410 |
| Colgate/Ab | 0.658 | 0.349 | 0.423 | 0.418 |
| Listerine/Ab | 0.136 | 0.050 | 0.063 | 0.041 |
| Hello/Ab | 0.650 | 0.425 | 0.470 | 0.404 |

TABLE 7A

Stability of anti-*P. gingivalis* antibody in mouthwash (1:150 dilution)

| Mouthwash | Day 1 | Day 16 | Day 72 | Day 84 |
|---|---|---|---|---|
| Buffer/Ab | 0.711 | 0.809 | 0.809 | 0.335 |
| ACT/Ab | 1.032 | 0.874 | 1.208 | 0.779 |
| Colgate/Ab | 0.845 | 0.785 | 1.245 | 0.764 |
| Listerine/Ab | 0.312 | 0.242 | 0.252 | 0.198 |
| Hello/Ab | 0.784 | 0.730 | 1.133 | 0.817 |

TABLE 7B

Stability of anti-*P. gingivalis* antibody in mouthwash (1:300 dilution)

| Mouthwash | Day 1 | Day 16 | Day 72 | Day 84 |
|---|---|---|---|---|
| Buffer/Ab | 0.503 | 0.557 | 0.557 | 0.192 |
| ACT/Ab | 0.592 | 0.475 | 0.806 | 0.383 |
| Colgate/Ab | 0.503 | 0.413 | 0.887 | 0.428 |
| Listerine/Ab | 0.222 | 0.138 | 0.201 | 0.132 |
| Hello/Ab | 0.413 | 0.459 | 0.740 | 0.393 |

The results in FIG. 4-8 illustrate that antibodies are stable in all of the mouthwashes except Listerine. Listerine has been indicated as having a high alcohol content which can be detrimental to the activity of the antibodies.

Example 4—Use of Anti-*C. albicans* Antibodies in Mouthwash

Case Report 1—

An individual was diagnosed with psoriatic arthritis and especially Wegener's Syndrome. This individual is a 60 year old man currently actively farming in the Midwest. The primary treatment for the disease included the use of the chemotherapeutic agent, methotrexate. Upon such treatment, this individual experienced severe Candidiasis (Thrush) of the mouth and throat. He was unable to swallow or drink due to the Candidiasis.

Aliquots of the egg powder were provided to the individual with instructions to add 1 teaspoon (~4.5 gm) to 4 oz (113 ml) of water 3-4 times per day. One teaspoon of the egg powder included about 18 mg of antibodies. The egg powder was a quadravalent mixture. Thus, about 25% of the antibody (about 4.5 mg) was against *C. albicans*. The antibody solution was used as a mouth wash/gargle each of the 3-4 times per day. The water/antibody solution remained in the mouth for a minimum of 2 minutes and then expelled, not swallowed.

The anti-*Candida albicans* antibodies bind with the organism and thus are removed from the oral cavity.

This individual's candidiasis was ameliorated within 36 hours. The mouthwash/gargle activity was continued for 5 days to lessen or remove any residual *Candida albicans* organisms which remained.

There were no other health issues at that time. Upon retreatment with methotrexate several months later, this individual again presented with Candidiasis. Once again, he used the egg antibody product to prepare an antibody-water solution to rinse the mouth and throat as above. The Candidiasis was cleared within 36 hours.

Case Report 2—

A second individual, a 91 year old woman presented with a mouth infection related to an empty tooth cavity and swollen lip. She refused physician care. The antibody-water solution was prepared for her as in case report 1. She used it as a mouthwash/gargle for 5 days. The swollen area and mouth was rinsed for at least 2 minutes, 3 times per day. All rinse solution was expelled. The swelling and soreness receded and was gone within 3 days.

Although the present invention has been described with reference to preferred embodiments, workers skilled in the art will recognize that changes may be made in form and detail without departing from the spirit and scope of the invention.

What is claimed is:

1. A method of reducing pathogenic infections in an animal, the method comprising:
    treating lymphatic tissue in the oropharynx and the nasopharynx of the animal with a tonsillar composition to reduce one or more disease causing entities from the lymphatic tissue, wherein the tonsillar composition comprises avian antibodies from eggs of hens inoculated with one or more of the disease causing entities, wherein the one or more disease causing entities are whole microorganisms and wherein the avian antibodies bind and/or neutralize the one or more disease causing entities, wherein the one or more disease causing entities are from the genus *Streptococcus, Staphylococcus, Hemophilus, Aerococcus, Porphrymonas* or combinations thereof, wherein the avian antibodies are partially purified antibodies from egg contents or unpurified antibodies in whole egg contents and wherein the avian antibodies are spray dried egg contents of the egg.

2. The method of claim 1 wherein the treatment comprises providing the composition in drinking water.

3. The method of claim 1 wherein the treatment comprises administering the composition for at least 10 days.

4. The method of claim 1 wherein spray dried egg contents comprise the avian antibody and the amount of spray dried egg contents administered is between about 0.5 g/head/day and about 1.0 g/head/day.

5. The method of claim 1 wherein the disease causing entity is *Streptococcus suis*, cellular components from *S. suis*, products from *S. suis* or combinations thereof.

6. The method of claim 1 wherein the lymphatic tissue comprises Waldeyer's tonsillar ring, mucosa-associated lymphoid tissue or combinations thereof.

7. The method of claim 1 wherein the composition reduces complications associated with infection from the disease causing entities.

8. The method of claim 7 wherein the complications comprise meningitis, arthritis, septicemia, endocarditis and/ or combinations thereof.

9. The method of claim 1 wherein the animals are porcine, bovine or human.

10. The method of claim 1 wherein the one or more disease causing entities are derived from bacteria, viruses, yeast, fungi or combinations thereof.

11. The method of claim 1 wherein the avian antibodies are spray dried egg contents, purified avian antibody, partially purified avian antibody, egg yolks or combination thereof.

12. A method of reducing one or more disease causing entities in the oral cavity of an animal, the method comprising:
    treating the oral cavity of the animal with a composition comprising avian antibodies from eggs of hens inoculated with one or more of the disease causing entities, wherein the one or more disease causing entities are whole microorganisms, herein the treatment comprises contacting the oral cavity with the composition to reduce disease causing entities from the oral cavity of the animal, wherein the one or more disease causing entities comprises *Porphyromonas gingivalis, Candida albicans, T. denticola, B. extructa* or combinations thereof, wherein the avian antibodies are partially purified antibodies from egg contents or =purified antibodies in whole egg contents and wherein the avian antibodies are spray dried egg contents of the egg.

13. The method of claim 12 wherein the treatment comprises providing the composition in a liquid with between about 0.3 grams per animal/day and 1.5 grams per animal per day of spray dried egg powder and wherein the treatment is administered for at least 14 days.

14. The method of claim 13 wherein the liquid is drinking water.

15. The method of claim 12 wherein the composition reduces complications associated with infection from the disease causing entities.

16. The method of claim 12 wherein the animals are human.

17. The method of claim 12 wherein the one or more disease causing entities are derived from bacteria, viruses, fungi or combinations thereof.

18. The method of claim 13 wherein the liquid is mouthwash.

19. The method of claim 1, wherein the avian antibodies are water extracted from the contents of the egg.

20. The method of claim 12, wherein the avian antibodies are water extracted from the contents of the egg.

\* \* \* \* \*

UNITED STATES PATENT AND TRADEMARK OFFICE
CERTIFICATE OF CORRECTION

PATENT NO. : 9,655,962 B2  
APPLICATION NO. : 14/211947  
DATED : May 23, 2017  
INVENTOR(S) : Bradley M. Mitteness et al.

Page 1 of 1

It is certified that error appears in the above-identified patent and that said Letters Patent is hereby corrected as shown below:

In Claim 12, Column 14, Line 65 delete "=purified", insert --unpurified--.

Signed and Sealed this  
Thirty-first Day of July, 2018

Andrei Iancu  
*Director of the United States Patent and Trademark Office*